United States Patent [19]
Leonard et al.

[11] Patent Number: 4,710,178
[45] Date of Patent: Dec. 1, 1987

[54] PRECISION INJECTION SYSTEM AND METHOD FOR INTRALIGMENTAL ANESTHESIA

[75] Inventors: Henri Leonard, Besancon; Michel Seigneurin, St.Cergues-Douvaine, both of France

[73] Assignee: Micro-Mega S.A., Besancon, France

[21] Appl. No.: 906,641

[22] Filed: Sep. 11, 1986

Related U.S. Application Data

[63] Continuation of Ser. No. 793,676, Oct. 31, 1985, which is a continuation-in-part of Ser. No. 547,768, Nov. 1, 1983, abandoned.

[30] Foreign Application Priority Data

Nov. 3, 1982 [FR] France ................................ 82 18546
Aug. 3, 1983 [FR] France ................................ 83 12932
Nov. 9, 1984 [FR] France ................................ 84 17226

[51] Int. Cl.⁴ ............................................. A61M 5/00
[52] U.S. Cl. ................................... 604/209; 604/232
[58] Field of Search ............... 604/207, 208, 209, 224, 604/241, 234, 239; 240, 232; 222/309, 391; 433/80

[56] References Cited

U.S. PATENT DOCUMENTS

| 881,469 | 3/1908 | Hale | 604/239 |
|---|---|---|---|
| 964,950 | 7/1910 | Allinger | 604/241 |
| 1,217,630 | 2/1917 | Powers | 604/218 |
| 1,569,961 | 1/1926 | Bauchert | 604/241 |
| 1,694,767 | 12/1928 | Cook | 604/234 |
| 4,444,560 | 4/1984 | Jacklich | 604/224 |

Primary Examiner—John D. Yasko
Attorney, Agent, or Firm—Robert E. Burns; Emmanuel J. Lobato

[57] ABSTRACT

A precision injection system and method for intraligmental anesthesia and the like having a syringe with a tubular handle portion to which are removably connectable individually tubular headpieces as a longitudinal extension thereof. The headpieces receive a carpule cartridge with semi-solid contents therein or with liquid injection contents monitored during injections through elongate windows on opposite sides of the headpieces. Provision is also made for injection of known composite materials the viscosity of which cannot be determined by standard viscosity measurement methods. A dosing plunger housed in the tubular handle portion in a retracted start position is activated by a servo-dosing lever and advances incrementally axially into a mounted headpiece for delivery of metered quantities of the contents of the carpule cartridge each time the servo-dosing lever is actuated. Provision is made for semi-automatic resetting of the dosing plunger to a retracted start position by depressing a resetting key and raising the syringe to a generally vertically raised position. The dosing plunger has a rack thereon activated by a ratchet cooperative with the servo-dosing lever so that a reduction in the normal pressure applied to the servo-dosing lever is effected in making the injections.

32 Claims, 18 Drawing Figures

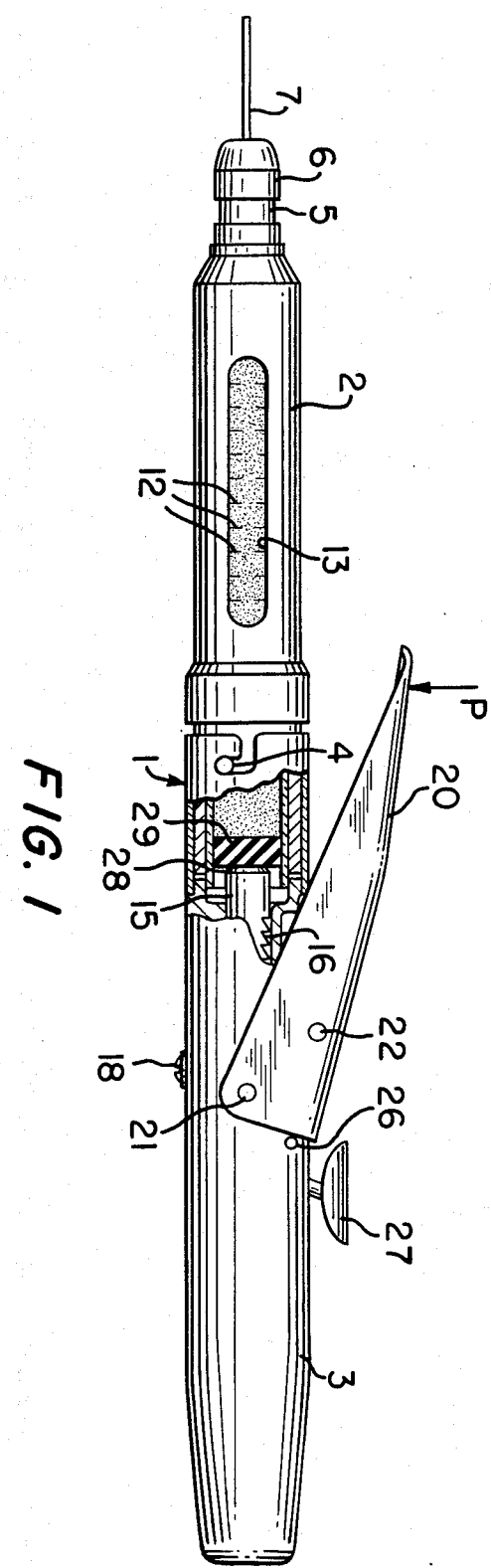

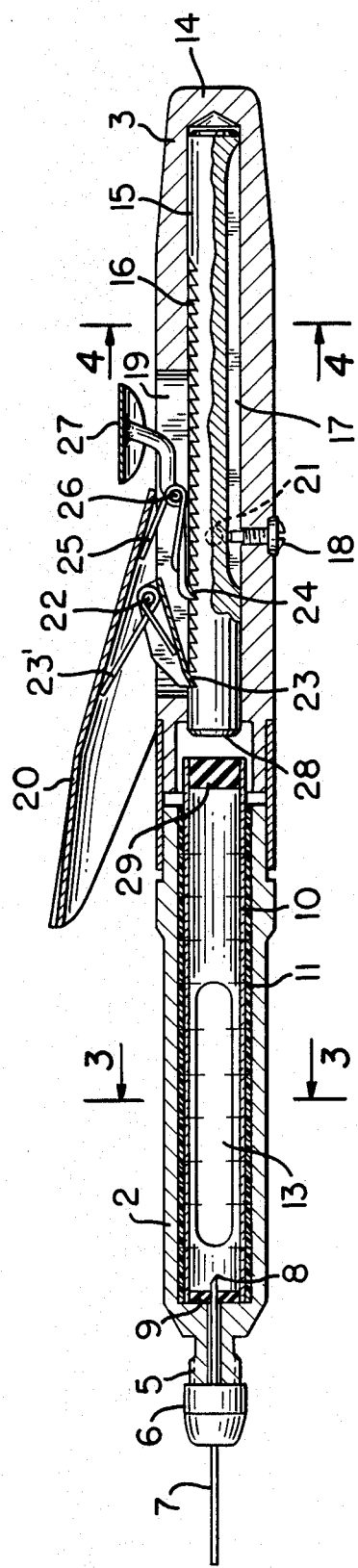
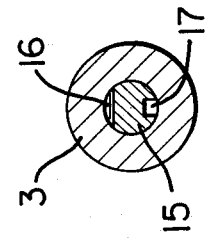
FIG. 4
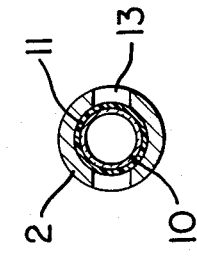
FIG. 2
FIG. 3

PRECISION INJECTION SYSTEM AND METHOD FOR INTRALIGMENTAL ANESTHESIA

This is a continuation Application Under Rule 62 of Ser. No. 793,676 filed Oct. 31, 1985, which is a continuation-in-part Application of Patent Application Ser. No. 547,768 filed Nov. 1, 1983, now U.S. Pat. No. 4,581,022.

BACKGROUND OF THE INVENTION

This invention relates generally to syringes and more particularly to a new and improved precision injection system having a metering syringe.

Metering syringes are known. In our patent application, Ser. No. 547,768 filed Nov. 1, 1983 we disclosed a precision injection system for intralignmental anesthesia and the like comprising a metering syringe. Our metering syringe and some other known syringes are able to variably deliver a fixed quantity or volume of injection material. The quantity of the injection is varied by varying the number of actuations of the delivery or activating mechanism of the syringe. Some known syringes, however, have a cumbersome structure for resetting the delivery components thereof and also are not easily monitored.

A dental metering syringe is disclosed in U.S. Letters Pat. No. 4,444,560 granted Apr. 24, 1984. The syringe disclosed therein may be calibrated so that each movement of the injection lever will discharge a known amount of liquid medication. This known device is without structure for ease of monitoring and ease of resetting. A calibrated hypodermic syringe determining and indicating the quantity of liquid administered is illustrated in U.S. Letters Pat. No. 201,443 dated Mar. 19, 1978. Both of these known syringes make use of the combination of a piston or plunger, of a pawl and rack for delivery of liquid medication or anesthesia. They can be actuated by one hand and the hypodermic syringe is also without resetting mechanism for the delivery mechanism.

Moreover, the known syringes are generally provided with a straight nozzle that is aligned with the longitudinal axis of the syringe. Such arrangements result in the known syringes not being as readily positionable so that the needle thereon can be readily directed into different angular injection positions without considerable manipulation and positioning of the syringe.

SUMMARY OF THE INVENTION

It is a principal object of the present invention to provide a precision injection system for intraligmental anesthesia.

The injection system has a precision syringe with a fountain pen-like design for performing precision intraligmental anesthesia and is capable of classical infiltration or block anesthesia. The syringe has a tubular body with a tubular handle portion and at least one exchangeable tubular headpiece. The precision injection system provides for a plurality of individual headpieces exchangeably mountable on the tubular handle. These are mounted coaxially with the tubular handle portion extending therefrom longitudinally for jointly therewith forming the syringe body. The tubular headpieces form a chamber within which is received and housed a carpule cartridge with contents therein to be injected. Each headpiece has elongate side windows so that the chamber functions as a viewing chamber for carpule control and monitoring. Each headpiece has a threaded nozzle for replaceably mounting thereon disposable, individual injection needles.

The activating mechanism for effecting injections is mounted on the tubular handle portions. A dosing plunger is housed in the handle position in a retracted position and a manually depressable servo-dosing lever is mounted externally on the tubular portion for activating the dosing plunger for incremental gradual advancing movement thereof. The dosing plunger movement is step-by-step axially out of the handle portion from its starting position into the headpiece at each depression of the servodosing lever to effect delivery of metered quantities of the contents of the carpule cartridge for flow out through the needle point of the injection needle depending upon the incremental axial travel of the dosing plunger.

Provision is made on the handle portion for quickly and easily resetting the dosing plunger to its retracted starting position for readiness for delivery of the contents of a next carpule cartridge. A resetting key on the handle portion is manually actuatable for semi-automatic retraction of the dosing plunger to its retracted initial or starting position when the syringe is held in a generally vertical position.

The precision injection system provides embodiments of headpiece with an angled nozzle and in particular a contra-angle nozzle with which special hypodermic short needles are used for intraligmental anesthesia. With this latter syringe embodiment dental anesthesia is readily accurately accomplished in a multiplicity of positions angularly of the longitudinal axis of the tubular syringe.

BRIEF DESCRIPTION OF THE DRAWING

Other features and advantages of the precision injection system according to the invention will be understood and made apparent by the following description, claims and appended drawing in which:

FIG. 1 is a side view, partly in section of a syringe according to the invention;

FIG. 2 is an axial section view through a plane of symmetry of the syringe in FIG. 1;

FIGS. 3 and 4 are cross section views taken along section lines 3—3 and 4—4 of FIG. 2;

DESCRIPTION OF THE PREFERRED EMBODIMENTS

Figure 6:
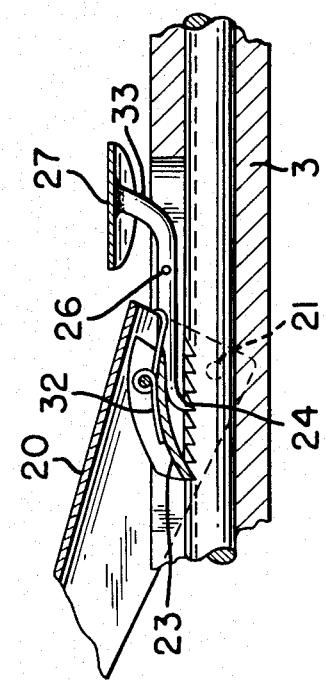
FIG. 6 is a fragmentary sectional view of another embodiment of the type syringe in FIG. 2.

An assembled syringe according to the present invention, is illustrated in FIG. 1. The assembled syringe 1 is made of a metallic tubular headpiece 2 removably connected to a metallic tubular handle portion 3. The two basic components are connected by a bayonet system or catch 4 and can be readily assembled and disassembled. The headpiece 2 has integral thereon a head nozzle 5 which is threaded to receive a threaded mount or adapter 6 of an injection needle 7 having an end 8 extending into the headpiece 2 and adapted to pierce a lid 9 sealing a front end of a glass carpule cartridge 10 housed in the headpiece and containing contents, for example a liquid, for injection with the syringe 1.

The headpiece 2 defines a viewing chamber within which are received and housed individual carpule cartridges 10 for individual injections. The headpiece 2 is detached from the tubular handle portion 3 and a carpule cartridge is introduced axially into a clear plastic sleeve 11 internally of the headpiece 2. The sleeve extends circumferentially and axially over the carpule cartridge. The headpiece is dimensioned to receive and completely house or hold the carpule cartridge therein. The clear plastic sleeve 11 has axially spaced graduation markings 12 thereon viewed through elongate windows 13 on opposite sides of the viewing chamber for monitoring the carpule cartridge and progress of the injections. The plastic sleeve will retain any glass splintering in case of breakage of a glass carpule cartridge.

The tubular handle portion 3 houses therein a dosing plunger 15 having an axial rack 16 with teeth disposed axially on an upper surface thereof. The dosing plunger is kept from rotating circumferentially in the handle portion by an axial guide groove 17 thereon into which extends a screw 18 fixed on the handle portion 3. The tubular handle portion is provided with activating means coactive with the dosing plunger through an opening 19 for effecting injections through the point of the needle 7 in dependence upon the incremental axial advancing movement of the dosing plunger.

The activating mechanism has a servo-dosing lever 20 pivotal on a pivot 21 fixed on the handle portion 3. The servo-dosing lever is made so that it has two opposite sides pivoted on its pivot 21. The servo-dosing lever extends forwardly in the direction of the headpiece 2 when the latter is mounted on the tubular handle portion 3. A pivot 22 mounted in the activating lever 20, extending between the two sides of the servo-dosing lever, has mounted thereon an activating ratchet or pawl 23 which engages the teeth of the rack 16 successively each time the servo-dosing lever is depressed. A spring 23' biases the servo-dosing lever upwardly away from the handle portion to a rest position and returns the lever 20 to its raised start or ready rest position, shown in the drawing, after each manual depression of the lever for effecting an injection.

A detent or catch pawl or catch ratchet 24 is continuously biased by a biasing spring 25 pivoted on a pivot 26 of the catch pawl so that the catch end of the detent or catch engages the individual teeth of the rack 16 successively as it is advanced forwardly axially by the activating ratchet and servo-dosing lever. The detent ratchet 24 keeps the dosing plunger in its advanced positions to which it has been activated stepwise from its retracted rest position each time the servo-dosinglever is dpressed. With the headpiece 2 in a charged condition with the carpule cartridge therein the dosing plunger is in a retracted or start position in which it is completely housed in the tubular handle portion. It is advanced incrementally axially forwardly out of the handle portion to effect the injections in definite same increments of volume of injection liquid determined by the step-by-step axial travel of the dosing plunger. This axial travel is a function of the individual teeth dimensions of the rack. Each depression of the servo-dosing lever advances the rack one tooth. All the teeth are similarly configured and dimensioned. The activating mechanism mechanically multiplies a relatively light pressure P applied by the practitioner in depressing the servo-dosing lever 20 and thus the injection pressure is increased and held since the detent ratchet keeps the dosing plunger at its advanced axial positions so that it does not inadvertently retract. The injection pressure is high so that an injection can be carried out through extremely fine needles. The injections must be made into tight spaces such as those between teeth and jawbone. The advancing of the dosing plunger is visually monitored by viewing it through the elongate windows of the viewing chamber of the headpiece 2. The increments of axial advancement can be monitored in conjunction with the graduations 12 on the clear plastic sleeve 11 in the headpiece.

Once injection of the contents of the carpule cartridge have been completed the expended carpule cartridge must be discharged and the syringe recharged for other injections. In order for the syringe to be unloaded the dosing plunger, which is an advanced position extending into the headpiece 2, is retracted to its rest or start position in which it is completely housed in the tubular handle portion. The syringe according to the invention provides for easily semiautomatically retracting the dosing plunger 15.

The detent pawl has a resetting key 27 fixed thereon for manual depression thereof to effect release of the dosing plunger by the detent or catch 24. Upon depressing of the catch pawl or lever 24 resetting key 27, once, the catch pawl is lifted off of the rack teeth, the dosing plunger is free to retract. The assembled syringe is then disposed with the headpiece lifted upwardly and the dosing plunger slides automatically downwardly, backwardly to its retracted positions in the tubular handle portion.

With the dosing plunger 15 retracted the headpiece is disassembled from the handle portion 3 by a quick partial rotation thereof to release the bayonet catch. The expended carpule cartridge is removed or discharged and a new cartridge inserted in the headpiece for a next injection. The headpiece can be exchanged for another headpiece as herein described. It will be understood that the rack teeth and activating pawl 1 cooperate in only one direction, for advancing the rack step-by-step to incrementally axially advance the dosing plunger. The detent pawl 24 slides over the teeth as the rack is advanced forwardly and it cooperates with the teeth only in one direction, in precluding backward movement of the dosing plunger to a retracted position. The simplified activating and resetting mechanisms make for easy construction and operation of the syringe embodying the invention.

The dosing plunger 15 is made as a cylinder with different types of leading ends or heads 28 for engaging a rubber stopper 29 of a corresponding carpule cartridge 10 in the headpiece as described below. Moreover, different activating mechanisms and resetting mechanisms may be provided on the tubular handle portion as illustrated in FIGS. 5 and 6 in which similar reference numerals identify similar components to those heretofore described.

Figure 5:
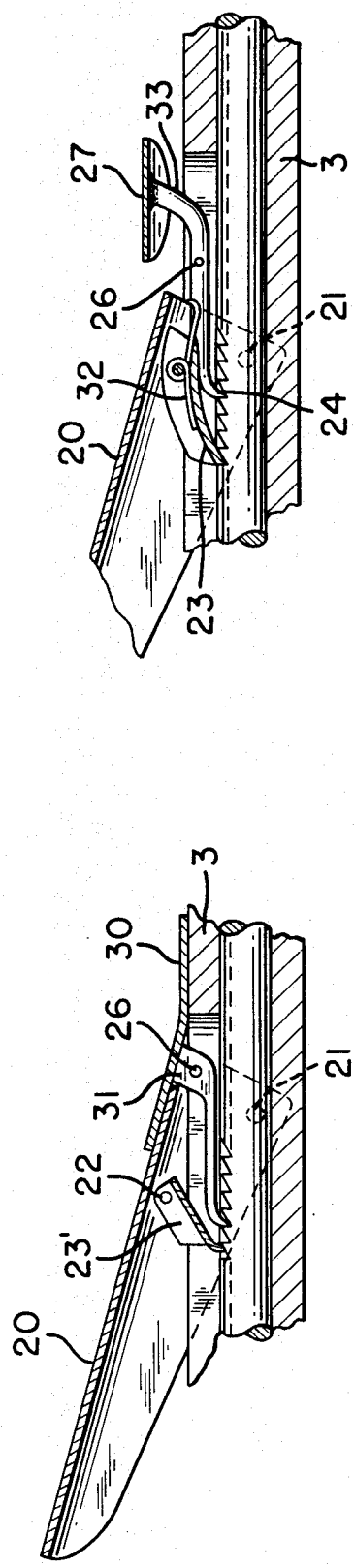
FIG. 5 is a fragmentary sectional view of an embodiment of a syringe according to the invention.

As illustrated in FIG. 5 the tubular hahdle portion 3 has a servo-dosing lever 20 mounted on a pivot 21. A spring strip 30 of flexible material such as a spring steel or semi-rigid plastic is fixed to an upper surface of the handle portion 3. This strip is bent as shown and is also attached to the servo-dosing lever 20. A pivot 22 on the servo-dosing lever pivotally mounts an activating pawl 23''. A detent ratchet 31 retains the dosing plunger from retracting. The spring strip 30 has memory and by depressing the servo-dosing lever the dosing plunger is incrementally advanced axially each time it is activated as before described as to the first embodiment. The spring strip restores the servo-dosing lever to its rest position each time after it is depressed and released. Since the spring strip 30 bears on the end of the catch lever 31 it constantly biases the catch into engagement with the teeth. Release of the catch 31 is effected by moving or lifting the dosing lever upwardly in a counterclockwise direction. Both pawls are thus released from the rack and the dosing plunger can then automatically retract when the assembled syringe headpiece is lifted to a raised position as before des- cribed.

Figure 6A:
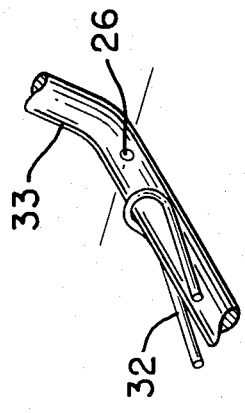

Another embodiment of the activating mechanism and resetting mechanism is illustrated in FIGS. 6 and 6a. In this embodiment the handle portion 3 has a servo-dosing lever 20 mounted on a pivot 21 and an activating pawl or ratchet 23 and a detent or catch pawl or ratchet 24 pivotal on a pivot. The latter ratchet has a resetting key 27. A staple spring 32 is mounted on the body 33 of the catch pawl. The staple spring is disposed to bias the servo-dosing lever to its raised rest position and bias both pawls 23,24 into engagement with the rack teeth. The servo-dosing plunger is advanced by depressing the servo-dosing lever 20 and the staple spring 32 restores the servo-dosing lever for axial incremental advancement of the dosing plunger rack. The two pawls 23,24 are released from the rack teeth by a single depression of the resetting key 27. Those skilled in the art will understand that the resetting key 27 and that the lever 20 can be activated at will to release the corresponding detents so that the closing plunger is released from its advanced positions so that the pressure applied to the carpule contents is released without removal of the injection needle; thereby avoiding any tissue damage from excess pressure being applied. The user of the syringe, for example, a dentist, can "feel" the backpressure, via the servo-closing lever, and release the detent to relieve any excess pressure. He need not remove the injection needle from the patient.

Figure 7:
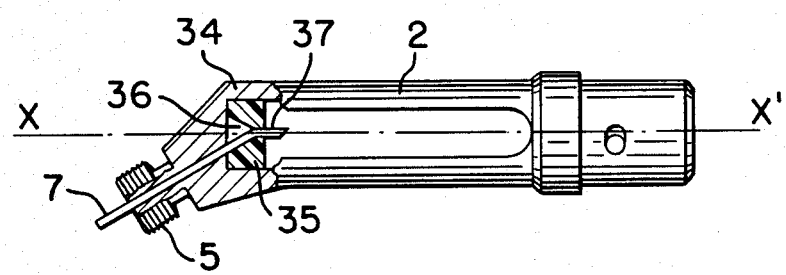
FIG. 7 is an enlarged perspective view of a detail of the syringe illustrated in FIG. 6.
Figure 8:
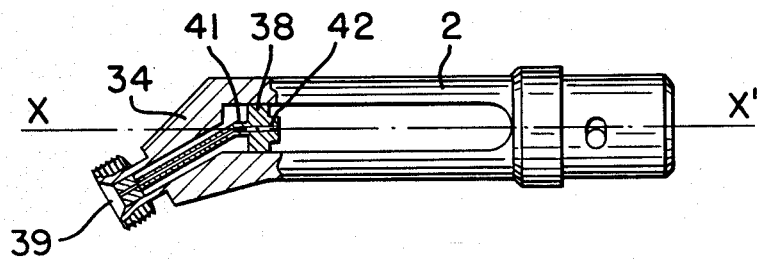
FIG. 8 is a side elevation view, partly in section, of a headpiece of a syringe according to the invention.

The injection system according to the invention makes provision for exchangeable headpieces mountable on the same tubular handle portion 3. Different embodiments of headpieces 2 with angled nozzles are illustrated in FIGS. 7 and 8 in which alike reference numerals are applied to similar parts to those already described. In FIG. 7 a headpiece has a longitudinal axis X-X' corresponding with the longitudinal axis of an elongate carpule cartridge, not shown, when housed in the headpiece. The headpiece has a fixed threaded nozzle 5 on an angled head 34. Within the headpiece at a front end of the viewing chamber is disposed a guide piece 35 made, for example, of a hard plastic preferably self-lubricating or of a suitable metal. This hard piece 35 has a funnel-shaped mouth or opening into which an injection needle 7 is mounted on the nozzle 5 by a threaded adapter, not shown. The funnel-shaped opening converges toward the axis of the viewing chamber space in the direction of the bayonet connection. As the injection needle enters the headpiece it is deflected and bent at its rear or entry end and is guided axially to the lid of the carpule cartridge, not shown, in the viewing chamber.

In the embodiment of a headpiece 2 illustrated in FIG. 8, an angled head 34 is shown. It is possible in practice that if the head 34 is very inclined relative to a longitudinal axis X-X' of the headpiece the rear or entry end 37 of a needle 7 will engage the funnel-shaped entrance at an excessive incident angle and the needle will be caught against the entrance or at least because of an improper bend will not be disposed axially of the longitudinal axis as desired.

To preclude this risk, the angled head 34 has a guide formed as a guide piece 38 which extends to a nozzle 39 as shown in FIG. 8. This guide is elongate and is bent as at 41. It extends through a channel in the head 34 and the bent portion is coaxial with the longitudinal axis X-X' of the headpiece. The internal guide piece 38 has a channel or passage 42. The channel is aligned with the axis X-X'. The internal guide piece can be made of metal or can be made of molded plastic. The channel 42 provides a guide path for an injection needle when mounted on the nozzle 39 so that the entry end of the needle will be properly disposed to eventually communicate with a carpule cartridge. The internal guide 38 can be held in place by adhering it to the headpiece, for example, with an adhesive.

Figure 9:
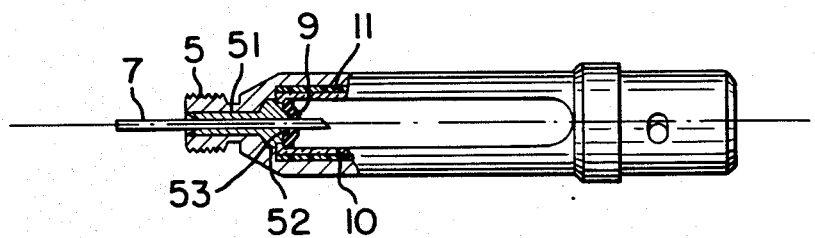
FIG. 9 is a side elevation view, partly in section, of another embodiment of a headpiece of a syringe according to the invention.
Figure 10:
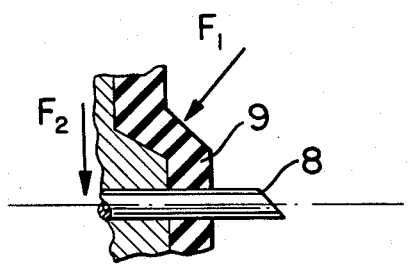
FIG. 10 is an enlarged sectional view of a detail of FIG. 9.

Other constructions of headpieces with needle guides are possible as shown in FIG. 9. A straight headpiece is illustrated having a nozzle 5 and in which a needle 7 is mounted piercing a rubber lid 9 of a carpule cartridge 10 internally of a clear plastic sleeve 11 in the viewing chamber of the headpiece. A guide sleeve 51 is mounted in the head of the headpiece for guiding introduction of an injection needle 7. The guide sleeve 51 has a cap 52 and a rear end funnel-shaped opening 53 into the headpiece.

The cap 52 presses the lid 9 around the injection needle 7. It prevents the lid from bulging under the pressure of the liquid contents when being injected, which could cause tearing of the lid. Moreover, the liquid pressure increases as the dosing plunger is advanced incrementally. The pressure can be resolved into an oblique pressure force $F_1$ and a radial force $F_2$. The latter acts in the direction of the needle 7. Thus in use, the entry or rear end 8 of the needle pierces the lid and its rupture or tearing is avoided and leakage of the liquid contents along the injection needle exterior surfaces is avoided since force components $F_2$ press the lid material circumferentially toward and about the needle to tend to effect a seal around the injection needle.

Figure 11:
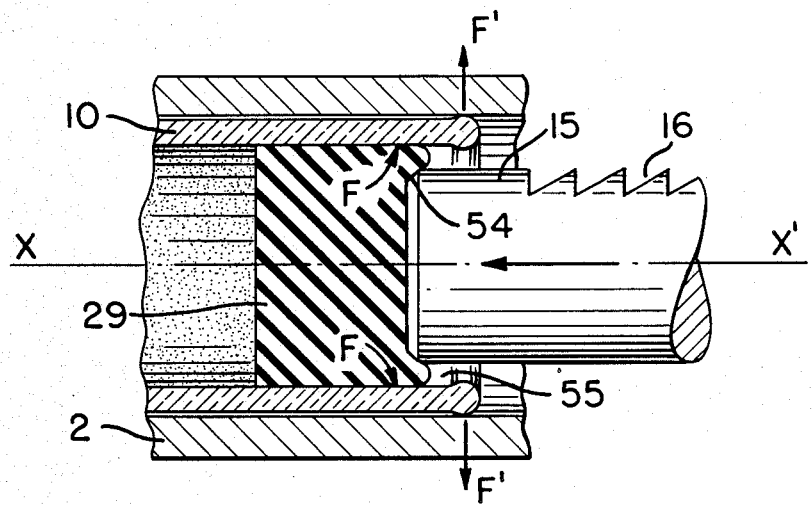
FIG. 11 is a fragmentary sectional view, on an enlarged scale, of a syringe dosing plunger according to the invention.
Figure 12:
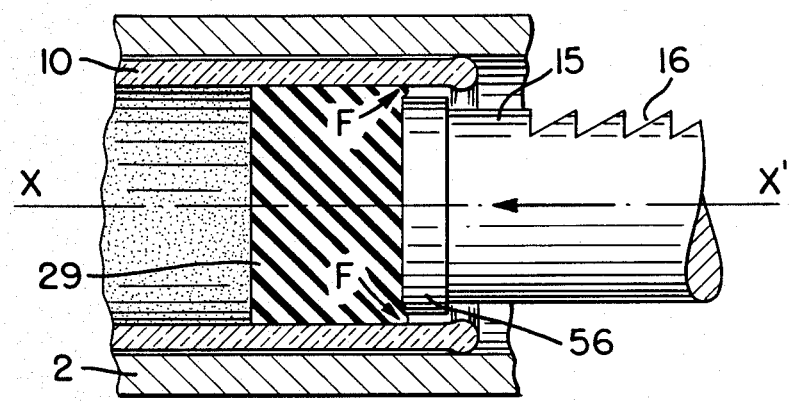
FIG. 12 is a fragmentary sectional view, on an enlarged scale of another embodiment of a syringe dosing plunger according to the invention.
Figure 13:
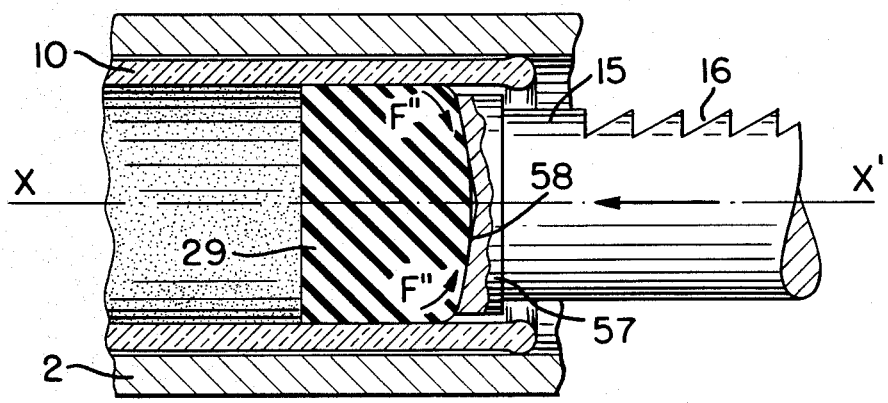
FIG. 13 is a fragmentary sectional view of a dosing plunger.

The head 28 of the dosing plunger engages the rubber stopper of the carpule cartridge 10 and the provision is made in the syringes for avoiding rupture problems as shown in FIGS. 11, 12 and 13. In these FIGS. the clear plastic sleeve 11 is not shown in order to simplify the drawing. In the FIGS. 1 to 4, the dosing plunger is of the type illustrated in FIG. 11. The dosing plunger therein is of lesser diameter than the diameter of the stopper 29 and has a beveled edge 54. The difference in diameter results in a clearance space 55 between the dosing plunger and the inner surface of a carpule cartridge. As the dosing plunger is advanced, force components F are developed in the stopper 29 so that a peripheral portion of the stopper tends to bulge and creep into the annular clearance space 55. The result is that outwardly directed force components F' are developed around the head of the dosing plunger tending to slow the dosing plunger and can result in breakage of the glass carpule cartridge.

To avoid this kind of problem, the dosing plunger can be constructed as shown n FIG. 12. The dosing plunger has a head 56 with an enlarged diameter of greater diameter than that of the dosing plunger. The clearance between the head 56 and the carpule cartridge is reeuced from the embodiment shown in FIG. 11. The force components F are developed but since the head 56 is about the diameter of the stopper 29 and the clearance reduced outward force component F' is a minimum since the bulging and creep before described are essentially avoided.

A third embodiment of a dosing plunger according to the invention is illustrated in FIG. 13. In this instance the plunger has a head 57 which has an enlarged diameter so that the head is about the diameter of the rubber stopper 29 of the glass carpule cartridge 10. In the embodiments of the dosing plungers in FIGS. 11 and 12 the leading face or surface of the respective heads are flat, substantially normal to the respective longitudinal axis X-X'. In this embodiment a leading surface or face 58 is concave. The concavity converges toward the longitudinal axis X-X'. Thus, as the dosing plunger is advanced and the rubber stopper 29 is compressed, pressure forces are developed. These forces, however, have a force component F'' applied toward the axis X-X' as illustrated and thus avoid the peripheral bulging and creep described above. Thus the outward force components are eliminated and there is no drag or braking of the piston and the bursting of the carpule cartridges is eliminated.

The embodiments of the headpieces heretofore described, relate to injection of liquid injections. The precision injection system embodying the invention makes provision for injection of pasty injection substances. These pasty substances are not contained in glass carpule cartridges but in containers with thicker walls. Moreover, in the headpieces used, means are provided to urge the dosing plunger toward a retracted position when the pasty substance has been completely expelled by injection.

Figure 14:
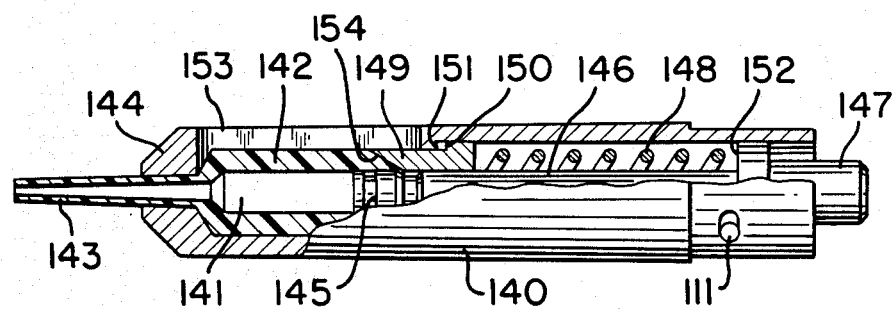
FIG. 14 is a side elevation view, partly in section, of a syringe headpiece for injection of pasty materials, according to the invention.
Figure 15:
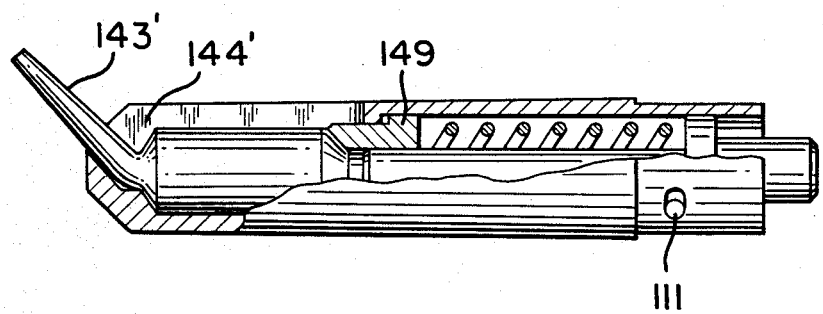
FIG. 15 is a side elevation view, partly in section, of another embodiment of a syringe headpiece for injection of pasty materials.

Headpieces for injection of pasty components are illustrated in FIGS. 14 and 15. As illustrated a headpiece 140 and has a bayonet system 111 for mounting on a tubular handle portion of the type before described. The headpiece 140 receives a pasty product 141 in a container which is a cylindrical body 142 with comparatively pressure-resisting walls. A tapered nozzle 143 extends from the front end or head 144 of the headpiece. The container 142 is closed at its rear end by a flexible stopper 145.

Within the headpiece is disposed an auxiliary dosing plunger 146 activated by a main dosing plunger 147 similar to the dosing plunger 15. The dosing plunger 147 has a head 152 which engages the auxiliary plunger when the headpiece is assembled with a tubular handle portion. The auxiliary plunger is urged rearwardly by a spring 148 compressed between a socket 149 slideable in the headpiece, and having a shoulder 150 engaging a corresponding shoulder 151 of the headpiece, and an enlarged head 152 of the main dosing plunger 147 when the headpiece is assembled on a handle portion.

The pasty injection material container 142 cannot be inserted axially into the headpiece because of the auxiliary dosing plunger 145. An elongate charging opening 153 is provided in the headpiece for introduction of the container 142 into place. The socket 149 has a beveled edge 154 to facilitate insertion of the container by retraction of the socket. The beveled edge keeps the container in place when the syringe is assembled.

The injection of pasty substances is accomplished by step-by-step advancement of the main dosing plunger 152 which advances the auxiliary plunger. The auxiliary plunger engages the stopper 145 of the container 142 and pushes it forwardly to expell the pasty injection contents through the nozzle 143. Such pasty products are injected into dental cavities and the syringe makes it easy to fill dental cavities, for example.

A different headpiece construction for delivery of pasty products is shown in FIG. 15 in which the headpiece has a head 144' in which an angled nozzle 143' can be mounted. The nozzle is oblique to the longitudinal axis of the headpiece. This type of construction is important because of the inaccessability of some areas of the buccal cavity for which use this headpiece is available.

Figure 16:
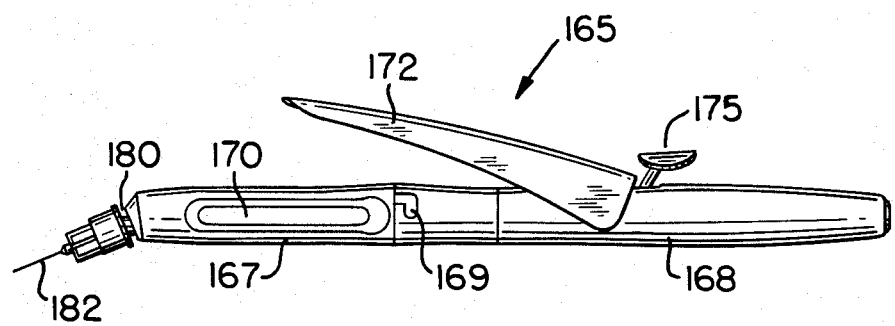
FIG. 16 is a side elevation view of a contra-angle embodiment of a syringe embodying the invention.
Figure 17:
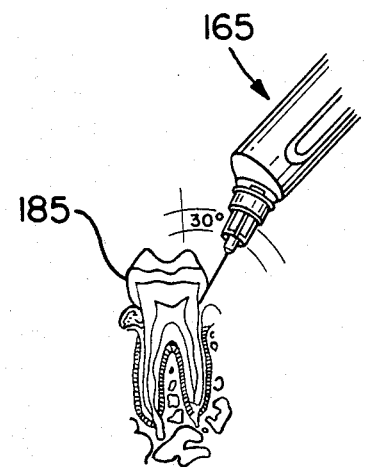
FIG. 17 is a fragmentary view of a syringe of FIG. 16 illustrating its use.

A particularly useful syringe for use in liquid injections is illustrated in FIGS. 16 and 17 as a contra-angle syringe 165. This syringe has a headpiece 167 connectable to a tubular handle portion 168 by a bayonet catch connection 169. The headpiece has elongate windows of a viewing chamber as described above for carpule cartridge control. Within the handle portion 168 is housed a dosing plunger which can have a head of an enlarged diameter, for example. The activating mechanism is as heretofore described and a servo-dosing lever 172 is provided and a resetting key 175 of the resetting mechanism.

This headpiece has an integral angled threaded nozzle 180 on the head of the headpiece. This provides a simple contra-angle nozzle for mounting a special hypodermic needle 182 on the nozzle, for example, for intraligmental anesthesia. Short or extra short needles provide a highly useful injection system. The injection system can be used to perform intraligmental anesthesia as opposed to infiltration or block anesthesia. This method injects the local anesthesia directly into the dental ligament (peridontal ligament).

As illustrated in FIG. 17, the needle point is apically inclined towards the central axis of a tooth 185. The needle point is inclined against the tooth (in case of a distal application, the needle might be slightly bent). The point of the needle is slowly introduced approximately at an angle of 30° and along the tooth 185 and the solution is simultaneously slowly injected by depression of the servo-dosing lever 172.

The syringe is also particularly suitable for the direct application of the following three groups of light hardening composite materials:

1. Macrofiller-composites containing 75 to 80% of inorganic filler, such as quartz or glass, and 20 to 25% of monomer, such as Bis-GMA, urethane monomer, etc. The average particle size is 10 $\mu$m and the maximum particle size is within the range of 50 to 70 $\mu$m.

2. Microfiller-composites containing 30 to 60% of inorganic filler, i.e. highly dispersed silica and 20 to 40% of monomer, partially prepolymers with and without highly dispersed silica as grinded polymer (particle size 10 to 80 $\mu$m) or bead polymer (particle size 5 to 60 $\mu$m). The primary particle size of the filler is 10 to 50 nm.

3. Hybrid-composites containing 75 to 85% of inorganic filler such as glass, glass ceramics or highly dispersed silica, having an average particle size of 1 to 5 $\mu$m and a maximum particle size in the range of 5 to 10 $\mu$m, and further containing 15 to 25% of monomer.

All the materials within groups 1 to 3 form a highly viscous kneadable and extrudable semi-solid mass, the viscosity of which is so high that it cannot be determined by standardized viscosity measurement methods. The syringe thus is quite versatile.

What we claim is:

1. A precision injection system for intraligmental anesthesia, filling of tooth cavities by injection, and the like comprising, an intraligmental syringe having a tubular handle portion and exchangeable tubular headpieces mountable on and dismountable from the handle portion for exchange thereof with other individual headpieces, means for removably and releasably mounting the headpieces individually coaxially with the tubular handle portion extending longitudinally therefrom for jointly defining therewith a tubular syringe, each headpiece having in use at an end thereof a nozzle, each headpiece defining a chamber for carpule control and dimensioned for receiving therein and containing a carpule cartridge with either liquid or compositions of a semi-solid mass contents therein to be injected, a dosing plunger housed in the handle portion in a retracted starting position, a servo-dosing lever mounted externally on the tubular handle portion for activating the dosing plunger for incremental gradual advancing movement axially out of said handle portion from the starting position into said chamber of the headpiece to effect delivery of metered quantities of contents of the carpule cartridge for flow through said nozzle in dependence upon the incremental axial advancing movement of the dosing plunger, activating means on the tubular handle portion coactive with the servo-dosing lever and dosing plunger for activating the dosing plunger incrementally each time the servo-dosing lever is depressed, and means comprising a resetting key on the handle portion actuatable manually for enabling semiautomatic retraction of the dosing plunger to the retracted starting position.

2. A precision injection system for intraligmental anesthesia filling of tooth cavities by injection, and the like according to claim 1, in which at least in some said headpieces said chamber thereof is an elongate viewing chamber having elongate windows therein for viewing and monitoring control of the carpule cartridge therein.

3. A precision injection system for intraligmental anesthesia, filling of tooth cavities by injection, and the like according to claim 2, in which an open-ended transparent sleeve is disposed axially internally of the headpiece, for viewing through said windows into the viewing chamber, and the sleeve being dimensioned to receive a carpule cartridge axially therein.

4. A precision injection system for intraligmental anesthesia, filling of tooth cavities by injection, and the like according to claim 3, in which said sleeve is resistant to splintering of individual glass carpule cartridges disposed therein during an injection.

5. A precision injection system for intraligmental anesthesia, filling of tooth cavities by injection, and the like according to claim 4, in which the sleeve has graduations axially spaced thereon for indicating the volume of said contents injected each time said servo-dosing lever is activated to advance the dosing lever step-by-step.

6. A precision injection system for intraligmental anesthesia, filling of tooth cavities by injection, and the like, according to claim 1, in which at least in one of the headpieces said chamber thereof is dimensioned to receive an elongate carpule cartridge for injection of non-liquid pasty contents therein, said headpiece having an elongate opening for introduction of the carpule cartridge into the headpiece.

7. A precision injection system for intraligmental anesthesia, filling of tooth cavities by injection, and the like according to claim 6, including an auxiliary dosing plunger in the headpiece actuated by said dosing plunger during advancement thereof under control of said servo-dosing lever, said auxiliary dosing plunger being disposed axially of the carpule cartridge for expelling said contents during an injection.

8. A precision injection system for intraligmental anesthesia, filling of tooth cavities by injection, and the like according to claim 7, in which said nozzle is on said carpule cartridge having said non-liquid, pasty contents.

9. A precision injection system for intraligmental anesthesia and the like comprising, an intraligmental syringe having a tubular handle portion and at least one exchangeable tubular headpiece mountable on and dismountable from the handle portion for exchange thereof with other individual headpieces, means for removably and releasably mounting the headpiece coaxially with the tubular handle portion extending longitudinally therefrom for jointly defining therewith a tubular syringe, the headpiece having at an end thereof a threaded nozzle for removably mounting individual replaceable injection needles each having a needle point, the headpiece defining a viewing chamber for carpule control and dimentioned for receiving therein and containing a carpule cartridge with contents therein to be injected, a dosing plunger housed in the handle portion in a retracted starting position, a servo-dosing lever mounted externally on the tubular handle portion for activating the dosing plunger for incremental gradual advancing movement axially out of said handle portion from the starting position into said viewing chamber of the headpiece to effect delivery of metered quantities of contents of the carpule cartridge for flow through the needle point of an injection needle in dependence upon the incremental axial advancing movement of the dosing plunger, activating means on the tubular handle portion coactive with the servo-dosing lever and dosing plunger for activating the dosing plunger incrementally each time the servo-dosing lever is depressed, means comprising a resetting key on the handle portion actuatable manually for enabling semiautomatic retraction of the dosing plunger to the retracted starting position, and at least one of said headpieces having said nozzle integral therewith extending coaxial with the corresponding headpiece and at least one of said headpieces having said nozzle integral therewith extending at an angle with the longitudinal axis of the corresponding headpieces.

10. A precision injection system for intraligmental anesthesia and the like according to claim 9, in which said dosing plunger is a cylinder and has a head at a leading end thereof having a diameter greater than the diameter of the cylinder.

11. A precision injection system for intraligmental anesthesia and the like according to claim 10, in which said head has a leading surface, and said leading surface being flat.

12. A precision injection system for intraligmental anesthesia and the like according to claim 10, in which said head has a leading surface, and in which said leading surface is concave.

13. A precision injection system for intraligmental anesthesia and the like according to claim 9, in which said threaded nozzle and said headpieces comprise guide means coactive to guide a needle during mounting thereon axially into the headpiece.

14. A precision injection system for intraligmental anesthesia and the like according to claim 9, including guide means in said chamber of individual headpieces, having an opening coaxial with a longitudinal axis of the corresponding headpiece for guiding the individual needles into said chamber of the corresponding headpiece coaxially therewith.

15. A precision injection system for intraligmental anesthesia according to claim 9, in which said opening on said guide means is funnel-shaped and having surfaces converging in a direction away from said nozzle.

16. A precision injection system for intraligmental anesthesia and the like according to claim 9, including a flexible strip having memory mounted on said tubular handle portion on an exterior surface thereof mounting said servo-dosing lever on said handle portion.

17. A precision injection system for intraligmental anesthesia and the like according to claim 16, in which said means for enabling semi-automatic retraction of the dosing plunger is effectively disenabled by said flexible strip, and is enabled by moving the servo-dosing lever in a direction opposite to the direction it moves when depressed.

18. A precision injection system for intraligmental anesthesia and the like comprising, an intraligmental syringe having a tubular handle portion and at least one exchangeable tubular headpiece mountable on and dismountable from the handle portion for exchange thereof with other individual headpieces, means for removably and releasably mounting the headpiece coaxially with the tubular handle portion extending longitudinally therefrom for jointly defining therewith a tubular syringe, the headpiece having at an end thereof a threaded contra-angle nozzle for removably mounting individual replaceable injection needles each having a needle point, the headpiece defining a viewing chamber for carpule control and dimensioned for receiving therein and containing a carpule cartridge with contents therein to be injected, a dosing plunger housed in the handle portion in a retracted starting position, a servo-dosing lever mounted externally on the tubular handle portion for activating the dosing plunger for incremental gradual advancing movement axially out of said handle portion from the starting position into said viewing chamber of the headpiece to effect delivery of metered quantities of contents of the carpule cartridge for flow through the needle point of an injection needle in dependence upon the incremental axial advancing movement of the dosing plunger, activating means on the tubular handle portion coactive with the servo-dosing lever and dosing plunger for activating the dosing plunger incrementally each time the servo-dosing lever is depressed, and means comprising a resetting key on the handle portion actuatable manually for semiautomatic retraction of the dosing plunger to the retracted starting position.

19. A precision injection system for intraligmental anesthesia and the like according to claim 20, in which the theaded contra-angle nozzle is unitary with the headpiece and in communication with the interior thereof and the contra-angle nozzle being angled relative to the longitudinal axis of the headpiece.

20. A precision injection system for intraligmental anesthesia and the like according to claim 18, in which said viewing chamber is elongate and has elongate windows axially thereon on opposite sides for viewing into the viewing chamber for carpule cartridge control.

21. A precision injection system for intraligmental anesthesia and the like according to claim 18, in which said means for removably and releasably mounting the headpiece coaxially with the tubular handle portion comprises a bayonet catch.

22. A precision injection system for intraligmental anesthesia and the like according to claim 18, including a plurality of other individual headpieces exchangeable on the tubular handle portion with the first-mentioned headpiece, each headpiece having an elongate viewing chamber for carpule control and each chamber having elongate windows axially thereon on opposite sides for viewing for carpule cartridge control.

23. A precision injection system for intraligmental anesthesia and the like according to claim 18, in which said dosing plunger has an axial rack thereon, and in which said actuating means comprises a ratchet engaging the rack on said dosing plunger actuated by said servo-dosing lever for advancing the dosing plunger axially incrementally.

24. A precision injection system for intraligmental anesthesia and the like according to claim 18, including a transparent tubular sleeve disposed axially in said viewing chamber for receiving individual carpule cartridges therein.

25. A precision injection system for intraligmental anesthesia and the like according to claim 24, in which said tubular sleeve comprises indicia thereon for monitoring the extent of axial advancement of said plunger and corresponding volume of delivery of said contents during injection.

26. A precision injection system for intraligmental anesthesia, filling of tooth cavities by injection, and the like comprising, an intraligmental syringe having a tubular handle portion and exchangeable tubular headpieces mountable on and dismountable from the handle portion for exchange thereof with other individual headpieces, means for removably and releasably mounting the headpieces individually coaxially with the tubular handle portion extending longitudinally therefrom for jointly defining therewith a tubular syringe, each headpiece having in use at an end thereof a nozzle, each headpiece defining a chamber for carpule cartridge control and dimensioned for receiving therein and holding a carpule cartridge with either liquid or compositions of a semi-solid mass contents therein to be injected, a dosing plunger housed in the handle portion in a retracted starting position, a servo-dosing lever mounted externally on the tubular handle portion for activating the dosing plunger for incremental gradual advancing movement axially out of said handle portion from the starting position into said chamber of the headpiece to effect delivery of metered quantities of contents of the carpule cartridge for flow through said nozzle in dependence upon the incremental axial advancing movement of the dosing plunger, activating means on the tubular handle portion coactive with the servo-dosing lever and dosing plunger for activating the dosing plunger incrementally forwardly each time the servo-dosing lever is depressed, detent means for releasably precluding retraction of the dosing plunger from axial positions as it is advanced incrementally, and means on the handle portion actuatable manually at will during use of the intraligmental syringe enabling said detent means to release pressure on the contents of the capsule cartridge being injected to avoid excess pressure during injections.

27. A precision injection system for intraligmental anesthesia, filling of tooth cavities by injection, and the like according to claim 26, in which said means on the handle portion for disenabling said detent means comprises a depressable resetting key coactive with said detent means.

28. A precision injection system for intraligmental anesthesia, filling of tooth cavities by injection, and the like according to claim 26, in which said means on the handle portion for disenabling said detent means comprises means actuated by the servo-dosing lever.

29. A precision injection system for intraligmental anesthesia, filling of tooth cavities by injection, and the like comprising, an intraligmental syringe having a tubular handle portion and exchangeable tubular headpieces mountable on and dismountable from the handle portion for exchange thereof with other individual headpieces, means for removably and releasably mounting the headpieces individually coaxially with the tubular handle portion extending longitudinally therefrom for jointly defining therewith a tubular syringe, each headpiece having in use at an end thereof a nozzle, each headpiece defining a chamber for carpule cartridge control and dimensioned for receiving therein and holding a carpule cartridge with contents therein to be injected, a dosing plunger housed in the handle portion in a retracted starting position, a servo-dosing lever mounted externally on the tubular handle portion for activating the dosing plunger for incremental gradual advancing movement axially out of said handle portion from the starting position into said chamber of the headpiece to effect delivery of metered quantities of contents of the carpule cartridge for flow through said nozzle in dependence upon the incremental axial advancing movement of the dosing plunger, activating means on the tubular handle portion coactive with the servo-dosing lever and dosing plunger incrementally each time the servo-dosing lever is depressed, means for releasably precluding retraction of the dosing plunger from axial positions as it is advanced incrementally, and means on the handle portion actuatable at will manually for disenabling the last-mentioned means for allowing retraction of the dosing plunger toward the retracted starting position including retraction effected by pressure internally of the carpule cartridge.

30. A precision injection syringe according to claim 29, in which said dosing plunger has a leading end having a leading face which is concave.

31. A precision injection syringe according to claim 30, in which said leading face has a concavity converging toward the longitudinal axis of the plunger.

32. A precision injection syringe according to claim 30, in which the concave face has a diameter for effectively engaging a rubber stopper of said carpule near the periphery thereof.

* * * * *